(12) United States Patent
Schuler et al.

(10) Patent No.: US 7,062,324 B2
(45) Date of Patent: *Jun. 13, 2006

(54) SPECIFIC METHOD FOR IMPLANTABLE CARDIAC CONTROL

(75) Inventors: Eleanor Schuler, Rio Rancho, NM (US); Claude K. Lee, Reno, NV (US)

(73) Assignee: Science Medicus, Inc., Albuquerque, NM (US)

( * ) Notice: Subject to any disclaimer, the term of this patent is extended or adjusted under 35 U.S.C. 154(b) by 65 days.

This patent is subject to a terminal disclaimer.

(21) Appl. No.: 10/797,391

(22) Filed: Mar. 10, 2004

(65) Prior Publication Data

US 2004/0230235 A1 Nov. 18, 2004

Related U.S. Application Data

(60) Provisional application No. 60/453,267, filed on Mar. 10, 2003.

(51) Int. Cl.
*A61N 1/362* (2006.01)

(52) U.S. Cl. .......................................................... 607/9

(58) Field of Classification Search ................ 607/2, 607/44, 62, 72–74, 9; 601/12, 153
See application file for complete search history.

(56) References Cited

U.S. PATENT DOCUMENTS

| | | | |
|---|---|---|---|
| 5,707,400 A * | 1/1998 | Terry et al. | 607/44 |
| 6,522,926 B1 * | 2/2003 | Kieval et al. | 607/44 |
| 6,681,136 B1 * | 1/2004 | Schuler et al. | 607/44 |
| 6,751,501 B1 | 6/2004 | Schuler et al. | |
| 2004/0236238 A1 * | 11/2004 | Schuler et al. | 600/513 |

* cited by examiner

*Primary Examiner*—Jeffrey R. Jastrzab
*Assistant Examiner*—Alyssa M. Alter
(74) *Attorney, Agent, or Firm*—Francis Law Group

(57) ABSTRACT

A method and device for modulating cardiac control. The method comprises selecting waveforms from a storage area that are representative of body organ function. The selected waveforms are then transmitted to a treatment member, which is in direct contact with the body, either internally or externally, and which then broadcasts the waveforms to a cardiac control regulatory points within the body to modulate cardiac pacing. A control module is provided for transmission to the treatment member. The control module contains the waveforms which are selected and transmitted to the treatment member, and computer storage can be provided for greater storage capacity and manipulation of the waveforms.

8 Claims, 2 Drawing Sheets

SPECIFIC METHOD FOR IMPLANTABLE CARDIAC CONTROL

RELATED APPLICATION

This is the non-provisional filing of application Ser. No. 60/453,267, filed on Mar. 10, 2003 entitled "Specific Method For Implantable Cardiac Control."

BACKGROUND OF THE INVENTION

It is said that an Australian physician and a physicist (both unnamed) reported that they had successfully revived a newborn's heart with an electrode on the skin and a needle electrode which was plunged into the baby's heart. That may have been the first successful defibrillation effort. In 1932, Albert Hyman, a New York cardiologist coined the term "pacemaker" for a device he designed to temporarily electrically stimulate patients hearts of hypothermia and shock patients. Then in 1947 a surgeon, Claude S. Beck, used his experimental defibrillator at the University Hospital in Cleveland, Ohio on a 14 year old boy during an open chest surgery to correct severe deformation of the rib cage. After the ribs were refashioned the patient's heart began fibrillating as the chest wall was being sutured closed. Dr. Beck reopened the chest to expose the fibrillating heart. He then used two electrodes directly on the heart to shock it with 1500 volts of alternating current. The boy recovered.

The field of using electricity to defibrillated and pace hearts took off in about 1950 when a Boston, Mass. physician, Paul Zoll, plunged wires through the skin and into the heart to allow his device to temporarily control the heart. Direct current was used in Dr. Zoll's devices rather then the alternating current used by Dr. Beck. Infection around the wires going through the skin, prevented any long term use of Dr. Zoll's device. Zoll founded Zoll Medical Corporation and developed a number of external pacer and defibrillator versions and brought them to market. All of them used simple high voltage waveforms and none of his models used natural codes.

In 1957 C. Walton Lillehei and Earl Bakken developed a wearable pacemaker with a sling carrier to hold a battery operated device with two electrodes pasted to the skin above the heart or which pierced the skin into the heart. In 1958 at the Karolinska Institute in Stockholm, Sweden a patient named Arne Larson received the first implantable pacemaker. It lasted only a few days but another was put in that lasted several weeks. The inventor Rune Elmqvist invented several improved models that kept Larson's heart beating. Over time 24 ever improved pacemakers by various manufacturers were implanted and the patient lived on into his 80s. None of the above used the natural body generated signals. All used high voltage contrived electrical waveforms.

Today, many models of small implantable pacemaker/defibrillators manufactured by a number of corporations have the ability to sense heart activity and automatically adjust electrical output to the heart to both pace and defibrillate. All of the electrical signals for internal devices are direct current powered and are generally 350 volts to 750 volts for defibrillation and usually start at the lower voltage and increase it during a successive three or four shocks. With each defibrillator shock the voltage is increased until the heart responds or the program reaches the highest output voltage. After a certain number of defibrillator shocks the electrodes implanted into the myocardium may burn the heart muscle and in effect char the tissue to such an extent that the electrodes must be moved to another area. This movement of electrodes to even-less-desirable places on the heart muscle in order to be effective. Over time, the patient can expect the defibrillation event to be less successful or not useful at all.

Pacing is a little more complicated in that some pacers use lower voltages to tickle a heart into compliance with relatively low voltages while other hearts need more powerful shocks to maintain a steady beat. Ostensibly implantable pacemakers are programmable through a variable range delivering approximately between 5 to 44 volts. However, it is not clear from manufacturer's claims what the actual delivered level of voltage or amperage is. All of these devices use simple electrical waveforms that bear no resemblance to the actual signals that operate the heart naturally. All natural signals that control the pacing rate are less than a volt. Voltage is not the entire story since impedance and current flow also play a part. The current expressed in amperage is greatly higher in all the state-of-the-art commercial pacemakers than natural currents. Natural amperage is in the order of milli or micro amps in the signal generating string of neurons which we call a nerve.

In general, medical product manufacturers guard voltage and current data which operate their implantable cardiac treatment products. They prefer that the public and the medical profession not know the real details on voltage and amperage levels. The waveforms used by all commercial implantable defibrillator/pacemakers are simple in form and bear no resemblance to the actual neuro coded signals used by natural human or animal cardiovascular systems. An example of waveforms found in some thorax implantable defibrillators consist of undamped capacitor discharge waveform or critically damped capacitor discharge (Edmark) or under-damped capacitor discharge (Lown) types. None of these waveforms resemble the natural neuro coded signals that naturally, from the beginning of life, operate & regulate cardiac operations.

The present invention relates to control of the heart, in particular defibrillation, pacing, and cardiac paralysis by means of an implantable device.

Existing devices for treating cardiac arrhythmia require deployment of high voltages which can, and often do, cause injury to the patient. The present invention permits utilization of low voltages and greatly decreases the risk of further injury to the patient. For example, the voltage required to propel the actual code through tissue and other barriers may be as high as 7 volts, but the actual code will be received by the heart or nerves controlling the heart typically at a range of less than one volt.

An arrhythmia is any abnormal electrical contraction of the heart. Particular arrhythmias include: asystole—no beat at all or "flat-line" on monitor; bradycardia—slow beat, less than 60 beats per minute; tachycardia—fast beat, over 100 beats per minute; and fibrillation—life threatening chaotic heart action in which the heart twitches or quivers rapidly and is unable to pump efficiently.

During fibrillation, less blood is circulating and thus all systems of the human or animal body are at risk. The longer fibrillation continues unchecked the more likely death will occur. For every minute of fibrillation, a 10% reduction of life potential is subtracted, i.e., ten minutes results almost certain death. During fibrillation the electrical system of the heart is disorganized and erratic. The normal rhythmic beat is totally lost. Serious life threatening events begin to occur. Breathing becomes erratic and then stops as electrical failure begins. Shortly the inadequate circulation of blood causes organs and tissues to be oxygen starved and cell death begins. When brain and heart muscle oxygen starvation reach crisis points they begin to die and hence the entire body begins to die. At some point the heart fibrillations are not reversible and death of the human or animal occurs. It is important to stop fibrillation and to restart or regain the same level of heart contractions to oxygenate the entire body properly.

Fibrillation is currently typically treated by an electronic defibrillator which delivers a shock via two hand-held paddles. This process is familiar to those who view medical television shows and witness a shock so great that the entire body jumps. This shock is about 1,800 to 5,600 volts for external shocks and 310 to 750 volts for internal defibrillators. Repeated use of such large electrical shocks likely may damage the nervous system to such an extent that disabilities shall be present even if the patient lives. The popular misconception is that a defibrillator "puts" a heart beat into a stopped heart. Actually, a defibrillator stops the quivering heart, after which, but not always, the heart may resume a slow beat (bradycardia). Paramedics then can use medications to speed up the heart and/or administer an emergency external pacemaker while transporting the victim to a hospital.

In the science of electromyography there is as graphical presentation of fibrillation on a visual monitor of a heart muscle being affected by a monophasic, biphasic or triphasic spike usually of 25 to 100 microvolts in amplitude and each less than 2 milliseconds in duration. These represent uncoordinated contractions of heart muscle (myocardium) fibers. This is a degrading and dangerous state and does require electrical intervention plus oxygen and cardiac medications in an effort to stabilize or regain a normal heart beat. Perhaps 40% of heart attack victims are in fibrillation when a paramedic arrives. Another 40% might be in bradycardia, tachycardia or asystolic status. The other 20% might have plugged heart blood vessels, bleeding, or other conditions that are not related to the electrical function of the heart muscle.

All individual organs of the body are electrochemical in nature and operate on something approximating one volt to conduct their respective duties. Certainly the action of the myocardium (muscular contractile body of the heart) which contracts about one billion times in a life span, also conducts its business of pumping blood utilizing only about one volt of electricity at any point in time. Each beat is a cascading flow of myocardial contractile motions that squeeze blood from the four chambers of the heart and then accept a refilling of blood for the next cycle.

The heart is a pump with a closed system of arteries and veins with a natural duty to circulate oxygenated blood over the entire network of blood vessels. Oxygenated blood is red when it is rich with oxygen loaded into its red cells, called erythrocytes. Blood turns blue as carbon dioxide ($CO_2$) and other waste products are loaded into its red cells, not now called "blue cells." The returning blue blood is pumped to the lungs to release the $CO_2$ and other gaseous waste products. The red cells immediately uptake oxygen and continue their journey via the heart and into the blood vessels, to cyclically do it all over again.

State of the art application of electricity for medical therapy to stop the fibrillation or quivering that is often encountered when a paramedic arrives on the scene of a heart attack victim, uses from 1,800 to 5,600 volts with 27 to 75 amps of current. The actual voltage and amperage that reaches the heart varies under Ohm's law by the resistance of the human or animal body and the integrity of electrode contacts to the body. Ohm's law states that voltage (V) equals the product of current (I) and resistance (R), or $V=IR$. Hydration of the skin under the electrodes also plays into the efficiency of the electrical therapy. There is approximately 50 to 150 ohms of resistance in the body depending on the hydration of live tissues. However, the most outer thin layer of dry skin can be 1000 to 30,000 ohms or higher. But high voltage can bust through that skin layer. Obviously the tissue is not as good a conductor as a metallic wire. However, because of the ionic nature of human or animal bodies it is possible to generate a specific waveform and cause it to enter the biological tissue and have an effect. Designers of external defibrillators anticipate a 50-ohm resistance load, but they know it could be somewhat higher. Internal implantable defibrillators/pacers operate in the highly conductive millei of the body inside the skin.

Despite public perception, most of the people collapsing with heart failure, are not reached in time by paramedics to save them. Those that live because they received early defibrillation are often impaired from the cardiopulmonary resuscitation (CPR) process or by the high-voltage energy applied to their chest. The use of voltages that are in the range of 1,800 to 5,600 volts applied to the closed-bare chest of a human is a risky event. It is also risky to the medical personnel who must stop all contact with the patient or potentially be an electrocution victim themselves. The patient must sustain the large shock which conducts all over the body, with risk of burning out peripheral nerves and injuring any organ or system. There is a question of why such large voltage electric shock therapeutically even makes a positive outcome in the small minority of heart attack victims it saves.

SUMMARY OF THE INVENTION

The invention provides a method for modulating cardiac pacing. Stored waveforms representative of waveforms that are generated and carried in the body are selected from a storage area. The selected waveforms are then transmitted to a treatment member which is in direct contact with the body. The treatment member then broadcasts the selected waveforms to an organ in the body.

The waveforms may be selected from a storage area in a computer, such as a scientific computer. The process of transmitting the selected waveforms can either be done remotely or with the treatment member connected to a control module. The transmission may be seismic, electronic, or via any other suitable method.

The invention further provides an apparatus for modulating cardiac pacing. The apparatus includes a source of collected waveforms that are indicative of body organ functioning, a treatment member formed to be in direct contact with the body, means for transmitting collected waveforms to the treatment member, and means for broadcasting the collected waveforms from the treatment member to a body organ.

The transmitting means may include a digital to analog converter. The source of collected waveforms preferably comprises a computer which has the collected waveforms stored in digital format. The computer may include separate storage areas for collected waveforms of different categories.

The treatment member may be comprised of an antenna or an electrode, or any other means of broadcasting one or more waveforms directly to the body. The treatment member may be implanted within the body.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
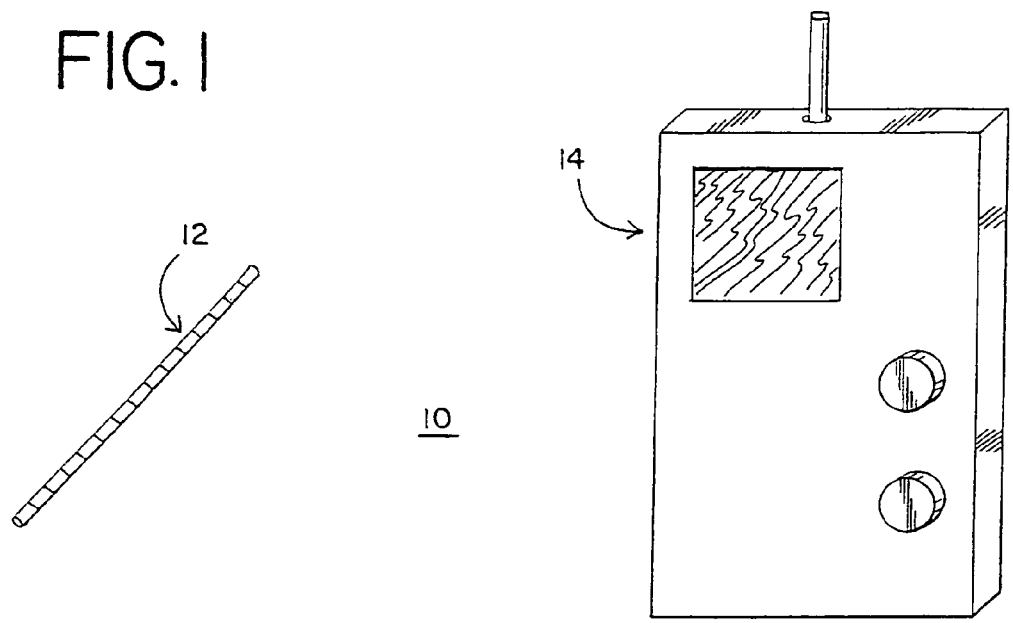
FIG. 1 is a schematic diagram of one form of apparatus for practicing the method according to the invention.

For the purpose of promoting an understanding of the principals of the invention, references will be made to the embodiments illustrated in the drawings. It will, nevertheless, be understood that no limitation of the scope of the invention is hereby intended, such alterations and further modifications in the illustrated device, and such further applications of the principals of the invention illustrated herein being contemplated as would normally occur to one skilled in the art to which the invention relates.

The invention consists of an implantable battery operated cardiac treatment device which utilizes the actual neuro coded signals that operate the cardiac system naturally.

The invention is a method to treat all arrhythmias (abnormal electrical contractions) of the heart. The method uses natural nerve signals that usually operate and regulate the heart throughout life. This includes treatment modalities for defibrillation, tachycardia, bradycardia and other electrical disturbances. The method also is useful for restarting a heart in asystole (no organized beat of any kind).

The attachment points for implantable electrodes or sensing devices include the sinus node on the myocardium (heart muscle) located near the base of the large vein (vena cava) which supplies blood to right atrium. Other attachment points can be the atrioventricular node and the nerve bundle of His located within the heart muscle.

Additional important electrical connections for the implantable method is at the region of the carotid bifracation located in the neck. Connection for sending natural coded signals are required at the carotid body and the carotid sinus structures which may include attachments to the afferent nerves leaving such structures and traveling to the medullopontine command motor interneurons within the brainstem.

Connections for the implantable device may alternatively or also be made at the level of the Pons and medulla oblongata of the brainstem. One of these connections can be made at the presympathetic vasomotor neurons in the rostral ventrolateral medulla oblongata. Another connection can be made at the nucleus tractus solitarius, also located in the medulla oblongata.

Connections to the implantable treatment device can also be made at selected afferent or efferent fibers or regions of the vagus cranial nerve as it travels through the thorax from the medulla oblongata. Neuro code programming of the implantable device will provide a set of signals as needed to treat or regulate the heart.

The invention disclosed herein consists of a waveform receiver and generator to process neural signals to elucidate (make lucid or clear) present status and then to transmit new instructions to alter cardiac control for the benefit of the patient. The invention has the capability to modulate both endocrine and neural inputs that are involved in cardiac regulation. The invention is meant to work in concert with present medications initially but the invention may allow for resetting base cardiac pacing to such an extent that previously prescribed medications may be reduced or eliminated as a treatment modality.

The invention encompasses both a device and method for modulating cardiac control by electrical waveforms. One form of a device 10 used for modulating cardiac control by electrical waveforms, as shown in FIG. 1, is comprised of at least one treatment member 12, and a control module 14. The device used in this invention is described in greater detail in U.S. Pat. No. 6,681,136, issued Jan. 20, 2003, and entitled "Method to Modulate Blood Pressure By Electrical Waveforms," the disclosure of which is incorporated herein by reference.

Figure 2:
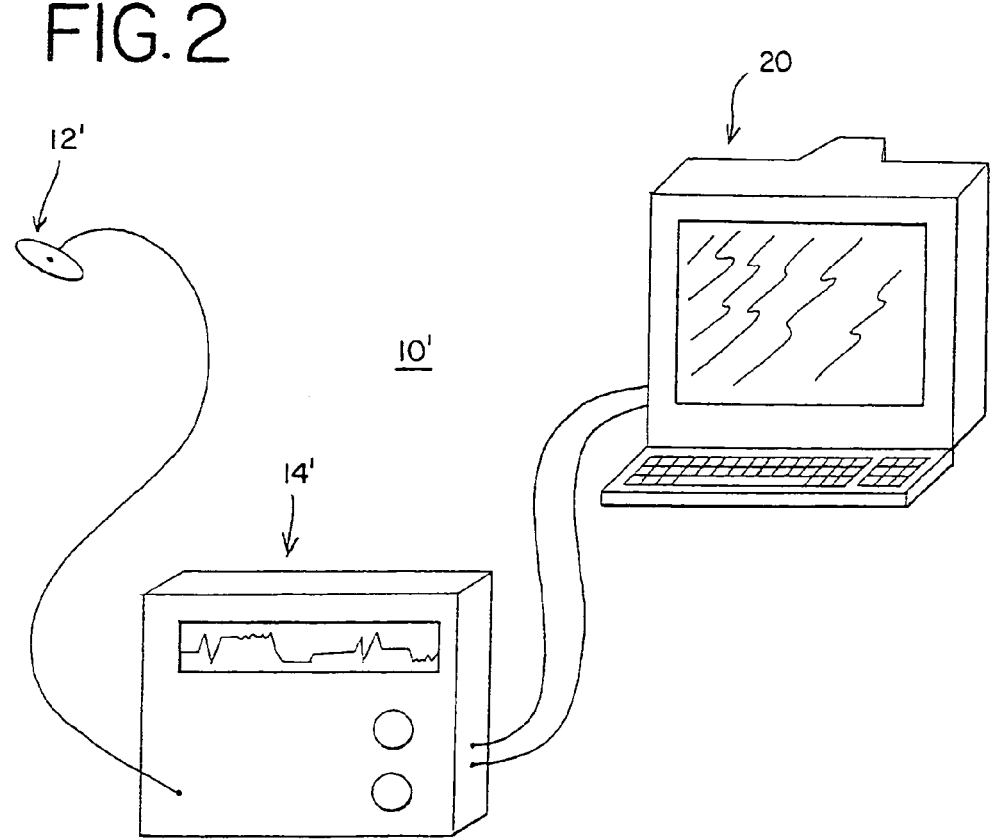
FIG. 2 is a schematic diagram of another form of apparatus for practicing the method according to the invention.

In an alternate embodiment of the device 10, as shown in FIG. 2 and as described in greater detail in the above patent application incorporated herein by reference, a control module 14' and treatment member 12' are connected. Similar members retain the same reference numerals in this figure. Additionally, FIG. 2 further shows another embodiment of the device 10' as being connected to a computer 20, which provides greater capacity to store the waveform signals. The computer 20 is used to store the unique waveform signals which are complex and unique to each organ and function of the organ.

Figure 3:
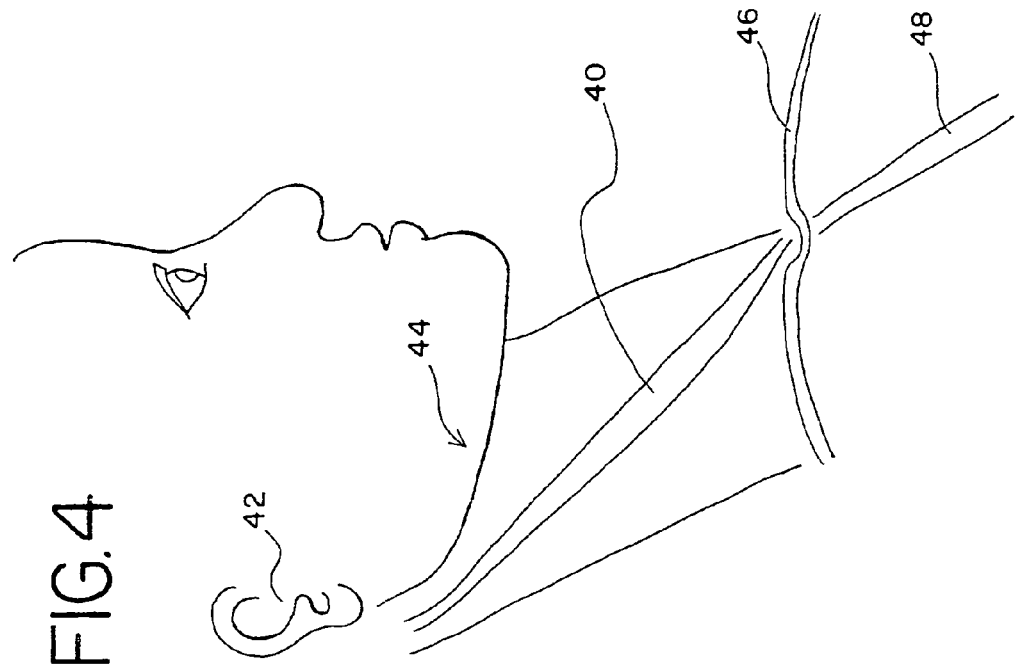
FIG. 3 is a flow chart of the method according to the invention.
Figure 4:
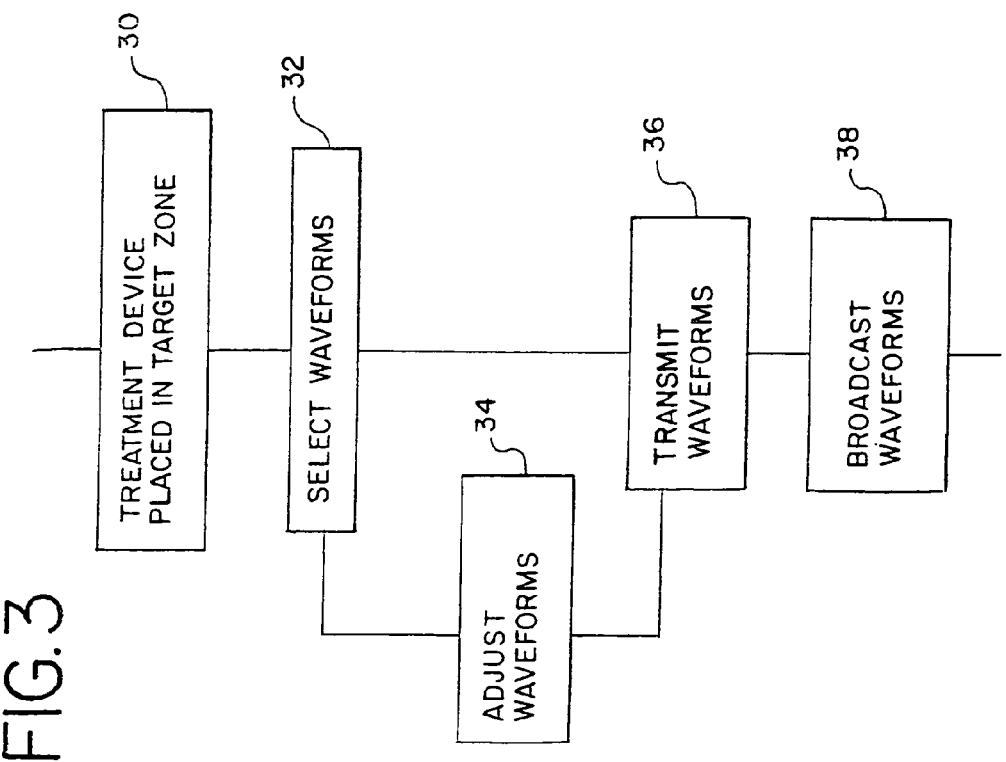
FIG. 4 is a schematic diagram of one of the cardiac pacing regulatory points treated by the invention.

The invention further includes a method, as shown in FIG. 3, for using the device 10, 10' to modulate cardiac control by electrical waveforms. The method begins at step 30 by placing the treatment member 12, 12' on a cardiac regulatory point 40, as shown in FIG. 4, which includes the area around the carotid body and carotid sinus between the angle of the jaw 44 at the ear 42 down to the clavicular notch, which is where the clavicular bone 46 meets the sternum 48. Alternatively, the cardiac regulatory point 40 can include appropriate afferent or efferent nerves connected to the aortic arch. Once the treatment member 12, 12' is placed on the target zone 40, at step 32 one or more stored electrical waveform signals are selected from a menu of catalogued waveform signals.

The waveform signals, and their creation, are described in greater detail in U.S. patent application Ser. No. 10/000,005, filed on Nov. 20, 2001, and entitled "Device and Method to Record, Store, and Broadcast Specific Brain Waveforms to Modulate Body Organ Functioning," the disclosure of which is incorporated herein by reference. Such application contains representative types of waveforms that are also operative in the control of human or animal cardiac pacing. Such waveforms or any combination of segments of the waveforms presented in the above mentioned provisional patent application are representative of the kinds of signals operating with neuron circuits emanating from the medullopontine region of the brain. Such waveforms can be used to modulate either afferent or efferent nerves that play a part in control or fine-tuning of cardiac pacing. Such waveform signals are similar to those naturally produced by the brain stem structures for modulating cardiac pacing, as described in greater detail in the immediately above-identified incorporated application.

Once selected, the waveform signals may be adjusted, step 34, to perform a particular function with respect to modulating cardiac pacing in the body. The actual adjustment forms no part of the present invention. Alternatively, if it is decided that the waveform signals do not need to be adjusted, step 34 is skipped and the process proceeds directly to step 36. At step 36, the waveform signal is transmitted to the treatment member 12, 12' of the device 10, 10'.

Upon receipt of the waveform signals, the treatment member 12, 12' in step 38 broadcasts the waveform signals to the target zone 40. The treatment member 12, 12' may be conventional, or may be specially developed just to transmit the unique waveform signals. The device 10, 10' utilizes appropriate waveform signals to modulate cardiac pacing via conduction or broadcast of electrical signals into the target zone 40.

In one embodiment of the invention, the process of broadcasting by the treatment member 12, 12' is accomplished by direct conduction or transmission through unbroken skin to the target zone 40. The target zone 40 will approximate a position close to the nerve or nerve plexus onto which the signal is to be imposed. The treatment member 12, 12' is brought into contact with the skin in the target zone 40 that allows for the transport of the signal to the target nerve.

In an alternate embodiment of the invention, the process of broadcasting the waveform is accomplished by direct conduction via implanting of an electrode to the receiving nerve or nerve plexus. This requires a surgical intervention as required to physically attach the electrode to the selected target nerve.

In yet another embodiment of the invention, the process of broadcasting is accomplished by transposing the waveform into a seismic form where it is sent into the target zone 40 in a manner that allows the appropriate "nerve" to receive and to obey the coded instructions of such seismic signal. The treatment member 12, 12' is pressed against the unbroken skin surface using an electrode conductive gel or paste medium to aid conductivity.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

We claim:

1. A method for modulating cardiac control in a body, comprising the steps of:
    providing a treatment member, said treatment member being adapted to be in communication with the body;
    providing a plurality of waveform signals representative of waveform signals generated in the body and carried by neurons in the body, said plurality of waveform signals being operative in the control of cardiac function, said plurality of waveform signals being stored in a storage medium;
    selecting at least a first waveform signal from said plurality of waveform signals;
    transmitting said first waveform signal to said treatment member; and
    broadcasting said first waveform signal from said treatment member directly to a cardiac regulatory point in the body.

2. The method of claim 1, wherein said storage medium comprises a memory region in a computer.

3. The method of claim 1, wherein said step of transmitting said first waveform signal comprises remotely transmitting said first waveform signal to said treatment member.

4. The method of claim 1, wherein said step of transmitting said first waveform signal comprises seismic transmission of said first waveform signal to said treatment member.

5. The method of claim 1, wherein said treatment member is adapted to be implanted within the body.

6. The method of claim 1, wherein said treatment member is adapted to be in contact with the body.

7. A method for modulating cardiac control in a body, comprising the steps of:
    providing a treatment member, said treatment member being adapted to be implanted in the body;
    providing a plurality of waveform signals representative of waveform signals generated in the body and carried by neurons in the body, said plurality of waveform signals being operative in the control of cardiac function;
    selecting at least a first waveform signal from said plurality of waveform signals;
    transmitting said first waveform signal to said treatment member; and
    broadcasting said first waveform signal from said treatment member directly to a cardiac regulatory point in the body.

8. The method of claim 7, wherein said cardiac regulatory point comprises a point selected from the group consisting of the vagus nerve, hypothalamus region of the brainstem, medulla region of the brainstem and medullopontine region of the brainstem.

* * * * *